United States Patent [19]

Wagner et al.

[11] Patent Number: 5,096,910

[45] Date of Patent: Mar. 17, 1992

[54] FUNGICIDAL NITRO-SUBSTITUTED BENZOTHIAZOLONES

[75] Inventors: Klaus Wagner, Cologne; Gerd Hänssler, Leverkusen; Wilhelm Brandes, Leichlingen, all of Fed. Rep. of Germany

[73] Assignee: Bayer Aktiengesellschaft, Leverkusen, Fed. Rep. of Germany

[21] Appl. No.: 504,151

[22] Filed: Apr. 2, 1990

[30] Foreign Application Priority Data

Apr. 7, 1989 [DE] Fed. Rep. of Germany ........ 3911226

[51] Int. Cl.$^5$ ............................................. A01N 43/78
[52] U.S. Cl. .................................. 514/367; 548/165; 548/172
[58] Field of Search ................. 548/172, 165; 514/367

[56] References Cited

FOREIGN PATENT DOCUMENTS

0218972  4/1987  European Pat. Off. .
0296416 12/1988  European Pat. Off. .
1100372  2/1961  Fed. Rep. of Germany .
2101150  3/1972  Fed. Rep. of Germany .

OTHER PUBLICATIONS

Klaus Wagner et al., "Über eine neue Synthese substituierter 2-Benzothiazolone", Chemische Berichte 107 (1974), pp. 305–315.
A. F. Aboulezz et al., "Conversion of (ortho-Nitrophenylthio) Acetic Acids", Egypt. J. Chem. 16 (1973), pp. 355–359.
JP-A6 0105-671, "Benzothiazolone deriv.-is used as agricultural fungicide etc. . . ", Ag. Chem., p. 7 (1985).
Chemical Abstracts, Band 104, Nr. 5, Feb. 3, 1986, Idemitsu Kosan Co. Ltd., "Benzothiazolones as fungicides", Siete 216, Spalte 2, Zusammenfassung-Nr. 30 422x & Jpn. Kokai Tokkyo Koho JP 60 105 604.
Chemical Abstracts, Band 103, Nr. 19, Nov. 11, 1985, Idemitsu Kosan Co. Ltd., "Benzothiazolinones", Seite 712, Spalte 2, Zusammenfassung-Nr. 160 499t & Jpn. Kokai Tokkyo Koho JP 60 105 671.

*Primary Examiner*—Robert Gerstl
*Attorney, Agent, or Firm*—Sprung Horn Kramer & Woods

[57] ABSTRACT

Combating fungi with nitro-substituted benzothiazolones of the formula

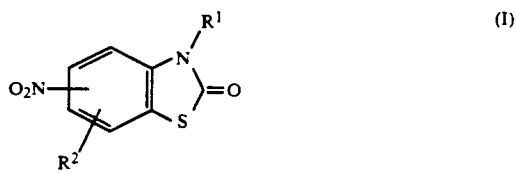

in which
$R^1$ represents hydrogen, alkyl, alkenyl or alkynyl, cycloalkyl-alkyl, furylalkyl, alkylcarbonyl which is optionally substituted by halogen or alkoxy, benzoyl which is optionally substituted by halogen, nitro, alkyl, halogenoalkyl and/or alkoxy, alkoxycarbonyl, phenoxycarbonyl, alkylaminocarbonyl which is optionally substituted by halogen or alkoxy, dialkylaminocarbonyl, benzyloxycarbonyl, benzylaminocarbonyl which is optionally substituted by halogen, alkyl, halogenoalkyl and/or alkoxy, or phenethylaminocarbonyl which is optionally substituted by halogen, alkyl, halogenoalkyl and/or alkoxy, and
$R^2$ represents hydrogen, halogen, alkyl or halogenoalkyl.

Some of the compounds and intermediates therefor are new.

3 Claims, No Drawings

FUNGICIDAL NITRO-SUBSTITUTED BENZOTHIAZOLONES

The present invention relates to the use of nitro-substituted benzothiazolones, some of which are known, as fungicides, to new nitro-substituted benzothiazolones and to processes for their preparation.

It has already been disclosed that certain plant diseases can be combated by cyclic sulphur compounds. Thus, for example, 6-methyl-2,3-quinoxalinedithiol cyclocarbonate (quinomethionate/Morestan) can be used against mildew in fruit cultivation (compare DE-.AS (German Published Specification) 1,100,372). However, the effect of this known compound, in particular at low active compound concentrations, is not always satisfactory.

Nitro- and/or trifluoromethyl-substituted benzothiazolones have furthermore been disclosed (cf. Chem. Ber. 107 (1974), 305–315; DE-OS (German Published Specification) 2,101,150), which likewise have a biological action.

It has now been found that the nitro-substituted benzothiazolones, some of which are known, of the general formula (I)

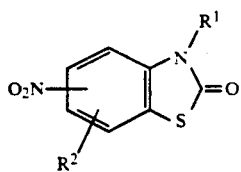

(I)

in which

R$^1$ represents hydrogen, alkyl, alkenyl or alkynyl, cycloalkyl-alkyl, furylalkyl, alkylcarbonyl which is optionally substituted by halogen or alkoxy, benzoyl which is optionally substituted by halogen, nitro, alkyl, halogenoalkyl and/or alkoxy, alkoxycarbonyl, phenoxycarbonyl, alkylaminocarbonyl which is optionally substituted by halogen or alkoxy, dialkylaminocarbonyl, benzyloxycarbonyl, benzylaminocarbonyl which is optionally substituted by halogen, alkyl, halogenoalkyl and/or alkoxy, or phenethylaminocarbonyl which is optionally substituted by halogen, alkyl, halogenoalkyl and/or alkoxy, and R$^2$ represents hydrogen, halogen, alkyl or halogenoalkyl, have strong fungicidal properties.

Surprisingly, the nitro-substituted benzothiazolones of the general formula (I) show a considerably stronger fungicidal action than structurally similar fungicides having a comparable profile of action, such as, for example, Morestan.

Aliphatic radicals such as alkyl, alone or in combinations, are straight-chain or branched, even if it is not expressly mentioned.

Halogen, alone or in combinations such as halogenoalkyl, denotes fluorine, chlorine, bromine or iodine, preferably fluorine, chlorine or bromine.

The invention preferably relates to the use of fungicidal agents based on compounds of the general formula (I), in which R$^1$ represents hydrogen, C$_1$–C$_{10}$-alkyl, C$_2$–C$_{10}$-alkenyl, C$_2$–C$_{10}$-alkynyl, cyclohexylmethyl, furylmethyl, C$_1$–C$_6$-alkyl-carbonyl which is optionally monosubstituted to pentasubstituted by identical or different substituents from the series comprising fluorine, chlorine and C$_1$–C$_4$-alkoxy, benzoyl which is optionally substituted by 1 to 3 identical or different radicals from the series comprising fluorine, chlorine, bromine, nitro, methyl, ethyl, trifluoromethyl, methoxy and ethoxy, C$_1$–C$_6$-alkoxy-carbonyl, phenoxycarbonyl, C$_1$–C$_6$-alkylamino-carbonyl which is optionally monosubstituted to trisubstituted by identical or different substituents from the series comprising fluorine, chlorine and C$_1$–C$_4$-alkoxy, di-(C$_1$–C$_4$-alkyl)-amino-carbonyl, benzyloxy-carbonyl, benzylaminocarbonyl which is optionally monosubstituted to trisubstituted by identical or different substituents from the series comprising fluorine, chlorine, bromine, methyl, ethyl, trifluoromethyl, methoxy and ethoxy, or phenethylaminocarbonyl which is optionally monosubstituted to trisubstituted by identical or different substituents from the series comprising fluorine, chlorine, bromine, methyl, ethyl, trifluoromethyl, methoxy and ethoxy, and R$^2$ represents hydrogen, halogen, C$_1$–C$_4$-alkyl or C$_1$–C$_1$-halogenoalkyl having 1 to 9 identical or different halogen atoms. Particularly preferably, the compounds of the formula (I) used are those according to the invention in which R$^1$ represents hydrogen, methyl, ethyl, propyl, isopropyl, butyl, isobutyl, pentyl, isopentyl, hexyl or isohexyl, allyl or propargyl, acetyl, propionyl, n- and iso-butyroyl, n-, iso-, sec.- and tert.-butylcarbonyl, n-, iso-, sec.- and tert.-pentyl-carbonyl, n-, iso-, sec.- and tert.-hexyl-carbonyl, trifluoroacetyl, chloroacetyl, dichloroacetyl, trichloroacetyl, bromoacetyl, α- and β-chloropropionyl, methoxyacetyl, ethoxyacetyl, benzoyl which is optionally substituted by 1 or 2 identical or different radicals from the series comprising fluorine, chlorine, bromine, nitro and methyl, methoxycarbonyl, ethoxycarbonyl, n- or iso-prop-oxycarbonyl, n-, iso- or sec.-butoxycarbonyl, methylaminocarbonyl, ethylaminocarbonyl, n- or iso-propylamino-carbonyl, n-, iso-, sec.- or tert.-butylaminocarbonyl,pentylaminocarbonyl,dimethylaminocarbonyl or diethylaminocarbonyl, benzyloxycarbonyl, benzylaminocarbonyl which is optionally substituted by 1 or 2 identical or different radicals from the series comprising fluorine, chlorine, methyl, trifluoromethyl and methoxy, or phenethylaminocarbonyl which is optionally substituted in the phenyl and/or alkyl radical by 1 or 2 identical or different radicals from the series comprising fluorine, chlorine, methyl, trifluoromethyl and methoxy, and R$^2$ represents chlorine, methyl or trifluoromethyl.

Examples of the compounds of the formula (I) to be used according to the invention are shown in Table 1 below.

TABLE 1

Examples of the compounds of the formula (I)

| Example No. | Position of NO₂ | R¹ | (Position) R² | Melting point (°C.) |
|---|---|---|---|---|
| 1 | 7 | —CO—CH₃ | (5-)CH₃ | 142 |
| 2 | 7 | —COOC₂H₅ | (5-)CH₃ | 140 |
| 3 | 5 | H | (7-)CH₃ | 250 |
| 4 | 7 | —CO—NH(CH₂)₂—⟨phenyl⟩ | (5-)CF₃ | 143 |
| 5 | 5 | —CO—CH₃ | (7-)CH₃ | 127 |
| 6 | 7 | —CO—CH₃ | (5-)CF₃ | 157 |
| 7 | 5 | —CO—NH(CH₂)₂—⟨phenyl⟩ | (7-)Cl | 230 |
| 8 | 5 | —CO—NHCH₂—⟨phenyl⟩ | (7-)CH₃ | 156 |
| 9 | 5 | —CO—NH(CH₂)₂—⟨phenyl⟩ | (7-)CH₃ | 151 |
| 10 | 5 | —CO—NHCH₂CH(Cl)—⟨phenyl⟩ | (7-)CH₃ | 155 |
| 11 | 7 | H | (5-)CH₃ | |
| 12 | 5 | —CO—C(CH₃)₃ | (7-)Cl | |
| 13 | 7 | —CO—CH₃ | (5-)Cl | 147 |
| 14 | 7 | —CO—C₂H₅ | (5-)Cl | 135 |
| 15 | 5 | —CO—C₂H₅ | (7-)CH₃ | 156 |
| 16 | 7 | —CO—C₂H₅ | (5-)CH₃ | 147 |
| 17 | 7 | —COOCH₂CH(CH₃)₂ | (5-)CH₃ | 87 |
| 18 | 7 | —CO—C(CH₃)₃ | (5-)CH₃ | 77 |
| 19 | 5 | CH₃ | (7-)CH₃ | 191 |
| 20 | 7 | CH₃ | (5-)CH₃ | 216 |
| 21 | 5 | —CO—NH(CH₂)₂CH(CH₃)₂ | (7-)Cl | 97 |
| 22 | 7 | —CO—NH(CH₂)₂CH(CH₃)₂ | (5-)Cl | 101 |
| 23 | 7 | —CO—NH(CH₂)₂—⟨phenyl-3,4-(OCH₃)₂⟩ | (5-)Cl | 125 |
| 24 | 7 | —CO—NHCH₂—⟨phenyl⟩ | (5-)Cl | 110 |
| 25 | 7 | CH₃ | (5-)Cl | 172 |
| 26 | 5 | —CO—NHCH(CH₃)₂ | (7-)Cl | 110 |

TABLE 1-continued

Examples of the compounds of the formula (I)

| Example No. | Position of $NO_2$ | $R^1$ | (Position) $R^2$ | Melting point (°C.) |
|---|---|---|---|---|
| 27 | 5 | —CO—NHCH₂—C₆H₅ | (7-)Cl | 113 |
| 28 | 5 | —CO—NH(CH₂)₂—C₆H₅ | (7-)CF₃ | 106 |
| 29 | 7 | —CO—NHCH₂—(2-Cl-C₆H₄) | (5-)CF₃ | 131 |
| 30 | 7 | —CO—NH(CH₂)₂CH(CH₃)₂ | (5-)CF₃ | 74 |
| 31 | 7 | —CO—NHCH₂—(3-OCH₃-C₆H₄) | (5-)CF₃ | 122 |
| 32 | 7 | —CO—NHCH₂—C₆H₅ | (5-)CF₃ | 115 |
| 33 | 5 | —CO—CH(CH₃)₂ | (7-)CH₃ | 143 |
| 34 | 5 | CH₃ | (7-)CF₃ | 126 |
| 35 | 5 | —CO—C₂H₅ | (7-)CF₃ | 106 |
| 36 | 5 | —CO—CH₂CH(CH₃)₂ | (7-)CF₃ | 105 |
| 37 | 5 | CH₃ | (7-)Cl | 176 |
| 38 | 7 | —CO—C₂H₅ | (5-)CF₃ | 100 |
| 39 | 7 | —CO—(CH₂)₅—CH₃ | (5-)CF₃ | 72 |
| 40 | 7 | —CO—(CH₂)₅—CH₃ | (5-)Cl | 80 |
| 41 | 5 | —CO—(CH₂)₅—CH₃ | (7-)CF₃ | 93 |
| 42 | 5 | —CO(CH₂)₅—CH₃ | (7-)CH₃ | 74 |
| 43 | 7 | —CO—NH(CH₂)₂—(3-F-C₆H₄) | (5-)CF₃ | 128 |
| 44 | 7 | —CO—NH(CH₂)₂—(3-OCH₃-C₆H₄) | (5-)CF₃ | 120 |
| 45 | 5 | —CO—NHCH₂—C₆H₅ | (7-)CF₃ | 116 |

TABLE 1-continued
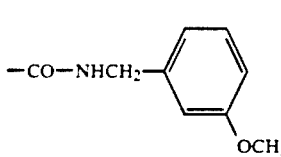
(I)
Examples of the compounds of the formula (I)
| Example No. | Position of NO₂ | R¹ | (Position) R² | Melting point (°C.) |
|---|---|---|---|---|
| 46 | 7 | CH₃ | (5-)CF₃ | |
| 47 | 5 | —CO—NHCH₂—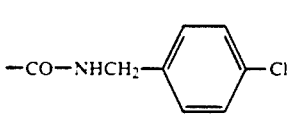—OCH₃ | (7-)CF₃ | 110 |
| 48 | 5 | —CO—CH₃ | (7-)Cl | 126 |
| 49 | 5 | —CO—(CH₂)₅—CH₃ | (7-)Cl | 78 |
| 50 | 7 | —CO—NHCH₂—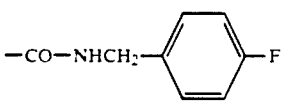—Cl | (5-)CF₃ | 130 |
| 51 | 7 | —CO—NHCH₂—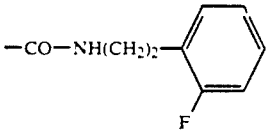—F | (5-)CF₃ | 142 |
| 52 | 5 | —CO—NH(CH₂)₂—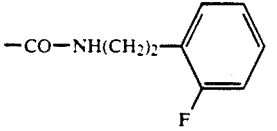 (F) | (7-)CF₃ | 121 |
| 53 | 7 | —CO—NH(CH₂)₂—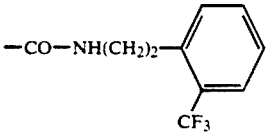 (F) | (5-)CF₃ | 134 |
| 54 | 5 | —CO—NH(CH₂)₂—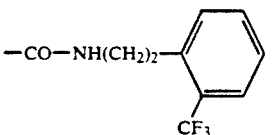 (CF₃) | (7-)CF₃ | 106 |
| 55 | 7 | —CO—NH(CH₂)₂— (CF₃) | (5-)CF₃ | 129 |
| 56 | 7 | —CO—(CH₂)₅—CH₃ | (5-)CF₃ | 97 |
| 57 | 5 | —CO—C₂H₅ | (7-)Cl | 137 |
| 58 | 6 | —CO—C₂H₅ | (7-)Cl | 85 |
| 59 | 7 | —CO—CH(CH₃)₂ | (5-)CH₃ | 97 |
| 60 | 6 | —CO—CH₃ | (7-)Cl | 129 |
| 61 | 6 | —CO—(CH₂)₅—CH₃ | (7-)Cl | 30 |

TABLE 1-continued $$\text{(I)} \quad \underset{R^2}{\underset{|}{O_2N}} \overbrace{\underset{S}{\bigcirc}}^{R^1} \!\!=\!\! O$$

Examples of the compounds of the formula (I)

| Example No. | Position of $NO_2$ | $R^1$ | (Position) $R^2$ | Melting point (°C.) |
|---|---|---|---|---|
| 62 | 7 | —CO—NHCH$_2$—(3-OCH$_3$-phenyl) | (5-)CH$_3$ | 138 |
| 63 | 7 | —CO—NHCH$_2$—(4-OCH$_3$-phenyl) | (5-)CH$_3$ | 160 |
| 64 | 7 | —CO—NH(CH$_2$)$_2$—(3-OCH$_3$-phenyl) | (5-)CH$_3$ | 135 |
| 65 | 7 | —CO—NHCH$_2$—phenyl | (5-)CH$_3$ | 138 |
| 66 | 7 | —CO—NH(CH$_2$)$_2$—phenyl | (5-)CH$_3$ | 153 |
| 67 | 6 | —CO—NHCH$_2$—phenyl | (7-)Cl | 124 |
| 68 | 7 | —CO—NHCH$_2$—(2-F-phenyl) | (5-)CF$_3$ | 106 |
| 69 | 7 | —CO—NHCH$_2$—(2,6-diF-phenyl) | (5-)CF$_3$ | 128 |
| 70 | 7 | —CO—NH(CH$_2$)$_2$—phenyl | (5-)Cl | 131 |

TABLE 1-continued $$\text{(I)}$$

Structure: benzothiazol-2(3H)-one with $O_2N$- and $R^2$ substituents on the benzene ring, and $R^1$ on the nitrogen.

Examples of the compounds of the formula (I)

| Example No. | Position of NO$_2$ | R$^1$ | (Position) R$^2$ | Melting point (°C.) |
|---|---|---|---|---|
| 71 | 7 | —CO—NHCH$_2$—(2-OCH$_3$-phenyl) | (5-)Cl | 157 |
| 72 | 7 | —CO—NHCH$_2$—(3-OCH$_3$-phenyl) | (5-)Cl | 144 |
| 73 | 7 | —CO—NHCH$_2$—(4-OCH$_3$-phenyl) | (5-)Cl | 145 |
| 74 | 7 | —CO—NH(CH$_2$)$_2$—(3-OCH$_3$-phenyl) | (5-)Cl | 125 |
| 75 | 7 | —CO—NHCH$_2$—(3-F-phenyl) | (5-)CF$_3$ | 100 |
| 76 | 5 | C$_2$H$_5$ | (7-)CF$_3$ | 112 |
| 77 | 5 | —CH$_2$—CH=CH$_2$ | (7-)CF$_3$ | 104 |
| 78 | 7 | —COO—phenyl | (5-)CH$_3$ | 152 |
| 79 | 6 | —CO—(2-F-phenyl) | — | 174 |
| 80 | 6 | —COCH$_2$CH(CH$_3$)$_2$ | (7-)Cl | 68 |
| 81 | 6 | —CO—CH(CH$_3$)$_2$ | (7-)Cl | 106 |
| 82 | 6 | —CO—(CH$_2$)$_5$—CH$_3$ | — | 80 |
| 83 | 5 | H | (7-)Cl | 248 |
| 84 | 7 | —CO—(2-F-phenyl) | (5-)CH$_3$ | 180 |

TABLE 1-continued

Examples of the compounds of the formula (I)

| Example No. | Position of NO₂ | R¹ | (Position) R² | Melting point (°C.) |
|---|---|---|---|---|
| 85 | 7 | —CO—(3-F-phenyl) | (5-)CH₃ | 156 |
| 86 | 7 | —CO—(2-F-phenyl) | (5-)Cl | 192 |
| 87 | 7 | —CO—(2-CF₃-phenyl) | (5-)CH₃ | 149 |
| 88 | 7 | —CO—phenyl | (5-)Cl | 156 |
| 89 | 7 | —CO—(4-F-phenyl) | (5-)Cl | 150 |
| 90 | 7 | —CO—(4-F-phenyl) | (5-)CH₃ | 188 |
| 91 | 6 | —CO—(2-CF₃-phenyl) | (7-)Cl | 163 |
| 92 | 5 | —CO—NH—CH₂—(2-F-phenyl) | (7-)CF₃ | 130 |
| 93 | 5 | —CO—NH—CH₂—(2,6-diF-phenyl) | (7-)CF₃ | 150 |

TABLE 1-continued
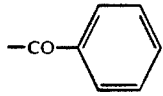
(I)
Examples of the compounds of the formula (I)
| Example No. | Position of NO$_2$ | R$^1$ | (Position) R$^2$ | Melting point (°C.) |
|---|---|---|---|---|
| 94 | 5 | 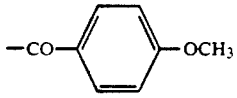 | (7-)CH$_3$ | 201 |
| 95 | 5 | 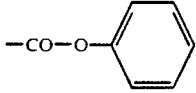 | (7-)CH$_3$ | 210 |
| 96 | 5 | 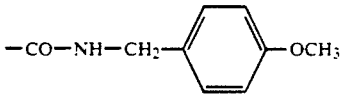 | (7-)CH$_3$ | 159 |
| 97 | 5 | 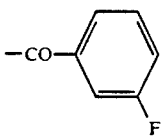 | (7-)Cl | 178 |
| 98 | 6 | 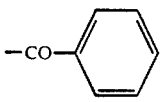 | (7-)Cl | (amorph) |
| 99 | 7 | 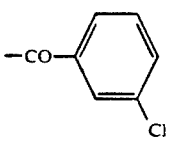 | (5-)CH$_3$ | 179 |
| 100 | 5 | 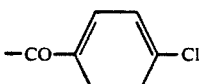 | (7-)CH$_3$ | 210 |
| 101 | 5 | 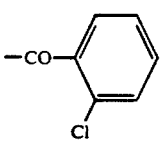 | (7-)CH$_3$ | 195 |
| 102 | 5 | 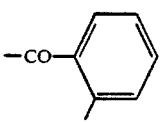 | (7-)CH$_3$ | 210 |
| 103 | 5 | —CO—⌬-F | (7-)CH$_3$ | 179 |

TABLE 1-continued

Examples of the compounds of the formula (I)

(I)

[Structure: benzothiazolone with $O_2N$, $R^1$ on N, =O, S, and $R^2$]

| Example No. | Position of NO₂ | R¹ | (Position) R² | Melting point (°C.) |
|---|---|---|---|---|
| 104 | 5 | —CO—C₆H₄—F (3-F) | (7-)CH₃ | 181 |
| 105 | 5 | —CO—C₆H₄—F (4-F) | (7-)CH₃ | 199 |
| 106 | 5 | —CO—C₆H₄—OCH₃ (3-OCH₃) | (7-)CH₃ | 167 |
| 107 | 5 | —CO—C₆H₄—CH₃ (3-CH₃) | (7-)CH₃ | 181 |
| 108 | 5 | —CO—C₆H₄—CH₃ (3-CH₃) | (7-)CF₃ | 155 |

The compounds of the formula (I) are known in some cases or can be prepared by methods which are known per se (cf. Chem. Ber. 107 (1974), 305–316; Egypt. J. Chem. 16 (1973), 355–359; JP-A 60-105 671; DE-OS (German Published Specification) 2,101,150; EP-A 218,972).

The present invention furthermore relates to new nitro-substituted benzothiazolones of the general formula (Ia)

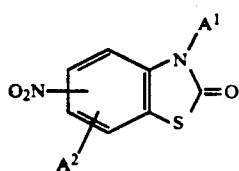

in which

A¹ represents alkyl, alkenyl or alkynyl, alkylcarbonyl which is optionally substituted by halogen or alkoxy-, benzoyl which is optionally substituted by halogen, nitro, alkyl, halogenoalkyl and/or alkoxy, alkoxycarbonyl, alkylamino-carbonyl which is optionally substituted by halogen or alkoxy, dialkylaminocarbonyl, benzyloxycarbonyl, benzylaminocarbonyl which is optionally substituted by halogen, alkyl, halogenoalkyl and/or alkoxy, or phenethylaminocarbonyl which is optionally substituted by halogen, alkyl, halogenoalkyl and/or alkoxy-, and A² represents alkyl.

The new compounds of the formula (Ia) are obtained when (a) nitro-substituted benzothiazolones of the general formula (II)

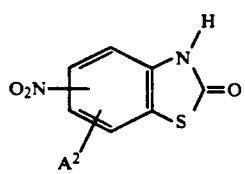

in which

A² has the abovementioned meaning, —or alkali metal salts of compounds of the general formula (II)— are reacted with halogen compounds of the general formula (III)

$$X^1-A^1 \quad (III)$$

in which

A$^1$ has the abovementioned meaning and

X$^1$ represents halogen, if appropriate in the presence of an acid acceptor and if appropriate in the presence of a diluent, or when (b) nitro-substituted benzothiazole-3-oxides of the general formula (IV)

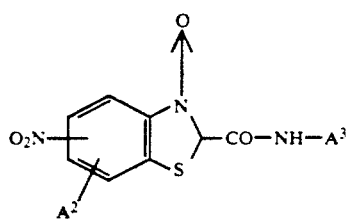

in which

A$^2$ has the abovementioned meaning and

A$^3$ represents alkyl optionally substituted by halogen or alkoxy, benzyl which is optionally substituted by halogen, alkyl, halogenoalkyl and/or alkoxy, or phenethyl which is optionally substituted by halogen, alkyl, halogenoalkyl and/or alkoxy, are reacted with phosphoryl chloride (POCl$_3$), if appropriate in the presence of a diluent.

The new and known compounds of the general formula (I) can be prepared in a manner which is the same in principle.

Preferred new nitro-substituted benzothiazolones of the formula (Ia) are those in which A$^1$ represents C$_1$-C$_{10}$-alkyl, C$_2$-C$_{10}$-alkenyl, C$_2$-C$_{10}$-alkynyl, C$_1$-C$_6$-alkyl-carbonyl which is optionally monosubstituted to pentasubstituted by identical or different substituents from the series comprising fluorine, chlorine and C$_1$-C$_4$-alkoxy, benzoyl- which is optionally substituted by 1 to 3 identical or different radicals from the series comprising fluorine, chlorine, bromine, nitro, methyl, ethyl, trifluoromethyl, methoxy and ethoxy, C$_1$-C$_6$-alkoxy-carbonyl, C$_1$-C$_6$-alkylaminocarbonyl which is optionally monosubstituted to trisubstituted by identical or different substituents from the series comprising fluorine, chlorine and C$_1$-C$_4$-alkoxy, di-(C$_1$-C$_4$-alkyl)-aminocarbonyl, benzyloxy-carbonyl, benzylaminocarbonyl which is optionally monosubstituted to trisubstituted by identical or different substituents from the series comprising fluorine, chlorine, bromine, methyl, ethyl, trifluoromethyl, methoxy and ethoxy, or phenethylaminocarbonyl which is optionally monosubstituted to trisubstituted by identical or different substituents from the series comprising fluorine, chlorine, bromine, methyl, ethyl, trifluoromethyl, methoxy and ethoxy, and A$^2$ represents C$_1$-C$_4$-alkyl.

Particularly preferred new compounds of the formula (Ia) are those in which

A$^1$ represents methyl, ethyl, propyl, isopropyl, butyl, isobutyl, pentyl, isopentyl-, hexyl or isohexyl, allyl or propargyl, acetyl, propionyl, n- and iso-butyroyl, n-, iso-, sec.- and tert.-butylcarbonyl, n-, iso-, sec.- and tert.-pentyl-carbonyl, n-, iso-, sec.- and tert.-hexyl-carbonyl, trifluoroacetyl, chloroacetyl, dichloroacetyl, trichloroacetyl, bromoacetyl, α- and β-chloropropionyl, methoxyacetyl, ethoxyacetyl, benzoyl which is optionally substituted by 1 or 2 identical or different radicals from the series comprising fluorine, chlorine, bromine, nitro and methyl, methoxycarbonyl, ethoxycarbonyl, n- or iso-propoxycarbonyl, n-, iso- or sec.-butoxycarbonyl, methylaminocarbonyl, ethylaminocarbonyl, n- or iso-prop-ylamino-carbonyl, n-, iso-, sec.- or or tert.-butylamino-carbonyl, pentylaminocarbonyl, dimethylaminocarbonyl or diethylaminocarbonyl, benzyloxycarbonyl, benzylaminocarbonyl which is optionally substituted by 1 or 2 identical or different radicals from the series comprising fluorine, chlorine, methyl, trifluoromethyl and methoxy, or phenethyla-minocarbonyl which is optionally substituted in the phenyl and/or alkyl radical by 1 or 2 identical or different radicals from the series comprising fluorine, chlorine, methyl, trifluoromethyl and methoxy, and A$^1$ represents methyl.

If, for example, 5-methyl-7-nitrobenzothiazolone and 4-fluoro-benzyl chloride are used as starting substances in process (a) for the preparation of the new and known compounds of the formulae (Ia) or (I), the course of the reaction can be represented by the following equation:

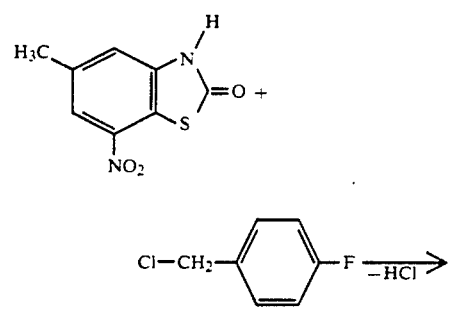

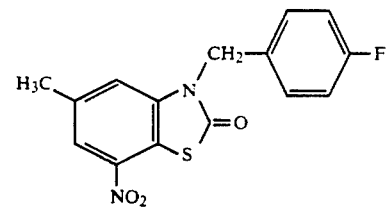

If, for example, 5-methyl-7-nitro-2-phenethylaminocarbonyl-benzothiazole-3-oxide and phosphoryl chloride are used as starting substances in process (b) for the preparation of the new or known compounds of the formulae (Ia) or (I), the course of the reaction can be represented by the following equation:

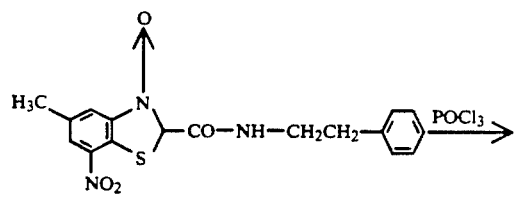

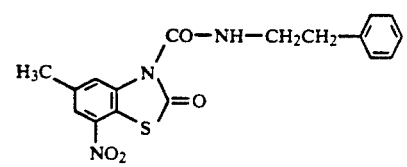

Formula (II) provides a general definition of the nitro-substituted benzothiazolones to be used as starting substances in process (a) according to the invention for the preparation of compounds of the formula (Ia).

In the formula (II), $A^2$ preferably or particularly has that meaning which has already been indicated above as preferred or as particularly preferred for $A^2$ in connection with the description of the compounds of the formula (I) according to the invention.

Examples of the starting substances of the formula (II) which may be mentioned are: 4-methyl-5-nitro-, 4-methyl-6-nitro-, 4-methyl-7-nitro-, 5-methyl-4-nitro-, 5-methyl-6-nitro-, 5-methyl-7-nitro-, 6-methyl-4-nitro-, 6-methyl-5-nitro-, 6-methyl-7-nitro-, 7-methyl-4-nitro-, 7-methyl-5-nitro- and 7-methyl-6-nitro-benzothiazolone.

The starting substances of the formula (II) are known in some cases or can be prepared by methods known per se (compare Egypt. J. Chem. 16 (1973), 355–359).

New starting substances are those of the formula (IIa)

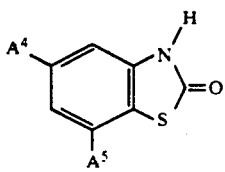

in which
one of the two substituents $A^4$ and $A^5$ in each case represents methyl and the other of the two substituents $A^5$ or $A^4$ represents nitro.

The active substances which are defined by the general formula (I) and which are used according to the invention include the starting substances of the formulae (II) and (IIa).

The new starting substances of the formula (IIa) are obtained when corresponding 2-carbamoyl-benzothiazole-3-oxides of the formula (V)

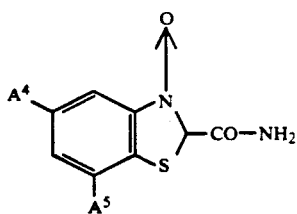

in which
$A^4$ and $A^5$ have the abovementioned meanings, are reacted with phosphoryl chloride (POCl$_3$), if appropriate in the presence of a diluent, such as, for example, toluene, at temperatures between 80° C. and 120° C.

The 2-carbamoyl-benzothiazole-3-oxides of the formula (V) have likewise not yet been disclosed in the literature. The new compounds of the formula (V) are obtained when corresponding 2-alkoxycarbonyl-benzothiazole-3-oxides of the formula (VI)

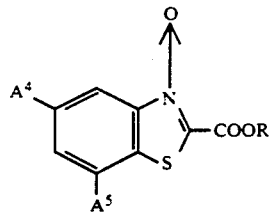

in which
$A^4$ and $A^5$ have the abovementioned meanings and
R represents alkyl, preferably having 1 to 4 carbon atoms, are reacted with ammonia in the presence of a diluent, such as, for example, water and/or methanol, at temperatures between 0° C. and 50° C.

The intermediates of the formula (VI) can also be used for the preparation of starting substances of the formula (IV) for process (b) according to the invention. The preparation of these and similar intermediates is described further below in connection with the description of the starting substances for process (b).

Formula (III) provides a general definition of the compounds further to be used as starting substances in process (a).

In formula (III), $A^1$ preferably or particularly has that meaning which has already been indicated above as preferred or as particularly preferred for in connection with the description of the compounds of the formula (Ia) according to the invention and $X^1$ preferably represents chlorine, bromine or iodine.

Examples of the starting substances of the formula (III) which may be mentioned are: methyl, ethyl, propyl, butyl, pentyl and hexyl chloride, bromide and iodide, isopropyl, isobutyl, isopentyl and isohexyl chloride and bromide, allyl and propargyl chloride and bromide, acetyl, propionyl, n- and isobutyroyl chloride, pivaloyl chloride, trichloroacetyl chloride, methoxyacetyl chloride, benzoyl- chloride, 2-fluoro-, 3-fluoro-, 4-fluoro-, 2-chloro-, 3-chloro-, 4-chloro-, 2-bromo-, 2-nitro-, 4-nitro- and 4-methylbenzoyl chloride, methyl and ethyl chloroformate and dimethylcarbamoyl chloride.

The starting substances of the formula (III) are known chemicals for organic synthesis.

Process (a) according to the invention for the preparation of the new or known compounds of the formulae (Ia) or (I) is preferably carried out using diluents. Possible diluents here are water and virtually all inert organic solvents. These preferably include aliphatic and aromatic, optionally halogenated hydrocarbons such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers such as diethyl ether and dibutyl ether, glycol dimethyl ether and diglycol dimethyl ether, tetrahydrofuran and dioxane, ketones such as acetone, methyl ethyl ketone, methyl isopropyl ketone and methyl isobutyl ketone, esters such as methyl acetate and ethyl acetate or nitriles such as, for example, acetonitrile and propionitrile.

Acid acceptors which can be used in process (a) according to the invention are all acid-binding agents customarily utilizable for reactions of this type. Those which are preferred are alkali metal hydroxides such as, for example, sodium hydroxide and potassium hydroxide, alkaline earth metal hydroxides such as, for example, calcium hydroxide, alkali metal carbonates and alkoxides such as sodium carbonate and potassium carbonate, sodium methoxide, ethoxide and tert-butoxide and potassium methoxide, ethoxide and tert-butoxide, and additionally aliphatic, aromatic or heterocyclic amines, for example triethylamine, trimethylamine, dimethylaniline, dimethylbenzylamine, pyridine,1,5-diazabicyclo-4.3.0]-non-5-ene (DBN), 1,8-diazabicyclo-[5.4.0]-undec-7-ene (DBU) and 1,4-diazabicyclo-[2.2.2]-octane (DABCO).

The reaction temperatures can be varied within a relatively- wide range in process (a) according to the invention. In general, the reaction is carried out at temperatures between $-20°$ C. and $+80°$ C., preferably at temperatures between $0°$ C. and $40°$ C.

Process (a) according to the invention is in general carried out under normal pressure.

In order to carry out process (a) according to the invention, the starting substances required in each case are in general employed in approximately equimolar amounts. However, it is also possible to use one of the two components employed in each case in a relatively large excess. The reactions are in general carried out in a suitable diluent in the presence of an acid acceptor and the reaction mixture is stirred for several hours at the temperature required in each case. Working up is in each case carried out by customary methods in process (a) according to the invention.

Formula (IV) provides a general definition of the nitro-substituted benzothiazole-3-oxides to be used as starting substances in process (b) according to the invention for the preparation of compounds of the formulae (Ia) or (I).

In the formula (IV), $A^2$ preferably or particularly has that meaning which has already been indicated above as preferred or as particularly preferred for $A^2$ in connection with the description of the compounds of the formula (Ia) according to the invention and $A^3$ preferably represents straight-chain or branched alkyl having 1 to 6 carbon atoms, which is optionally monosubstituted to trisubstituted by identical or different substituents from the series comprising fluorine, chlorine and $C_1$-$C_4$-alkoxy, benzyl which is optionally monosubstituted to trisubstituted by identical or different substituents from the series comprising fluorine, chlorine, bromine, methyl, ethyl, trifluoromethyl, methoxy and ethoxy, or phenethyl which is optionally monosubstituted to trisubstituted by identical or different substituents from the series comprising fluorine, chlorine, bromine, methyl, ethyl, trifluoromethyl, methoxy and ethoxy; in particular methyl, ethyl, propyl, isopropyl, butyl, isobutyl, sec-butyl, tert.-butyl, benzyl or phenethyl, which are optionally monosubstituted or disubstituted by identical or different substituents from the series comprising fluorine, chlorine, methyl, trifluoromethyl and methoxy.

Examples of the starting substances of the formula (IV) are shown in Table 2 below.

TABLE 2

Examples of the starting substances of the formula (IV)

(IV')

Structure: benzothiazole-3-oxide with $O_2N$ substituent, $A^2$ substituent, and $-CO-NH-A^3$ at the 2-position.

| Position of $NO_2$ | (Position) $A^2$ | $A^3$ |
|---|---|---|
| 5 | (7-)$CH_3$ | $CH_3$ |
| 7 | (5-)$CH_3$ | $CH_3$ |
| 5 | (7-)$CH_3$ | $C_2H_5$ |
| 7 | (5-)$CH_3$ | $C_2H_5$ |
| 5 | (7-)$CH_3$ | $C_3H_7$ |
| 7 | (5-)$CH_3$ | $C_3H_7$ |
| 5 | (7-)$CH_3$ | $C_4H_9$ |
| 7 | (5-)$CH_3$ | $C_4H_9$ |
| 5 | (7-)$CH_3$ | $C_5H_{11}$ |
| 7 | (5-)$CH_3$ | $C_5H_{11}$ |
| 5 | (7-)$CH_3$ | $C_6H_{13}$ |
| 7 | (5-)$CH_3$ | $C_6H_{13}$ |
| 5 | (7-)$CH_3$ | $CH_2-CH(CH_3)_2$ |
| 7 | (5-)$CH_3$ | $CH_2-CH(CH_3)_2$ |
| 5 | (7-)$CH_3$ | $C(CH_3)_3$ |
| 7 | (5-)$CH_3$ | $CH(CH_3)-CH_2-CH_3$ |
| 5 | (7-)$CH_3$ | $-CH_2-$phenyl |
| 7 | (5-)$CH_3$ | $-CH_2-$phenyl |
| 5 | (7-)$CH_3$ | $-CH_2CH_2-$phenyl |
| 7 | (5-)$CH_3$ | $-CH_2CH_2-$phenyl |
| 5 | (7-)$CH_3$ | $-CH_2-$(4-F-phenyl) |
| 7 | (5-)$CH_3$ | $-CH_2-$(3-Cl-phenyl) |
| 5 | (7-)$CH_3$ | $-CH_2-$(4-$CH_3$-phenyl) |

TABLE 2-continued

Examples of the starting substances of the formula (IV)

(IV)

| Position of NO$_2$ | (Position) A$^2$ | A$^3$ |
|---|---|---|
| 7 | (5-)CH$_3$ | —CH$_2$—C$_6$H$_4$—CF$_3$ |
| 5 | (7-)CH$_3$ | —CH$_2$—C$_6$H$_4$—OCH$_3$ |
| 7 | (5-)CH$_3$ | —CH$_2$—C$_6$H$_3$(OCH$_3$)$_2$ |
| 5 | (7-)CH$_3$ | —CH$_2$CH$_2$—C$_6$H$_3$(OCH$_3$)$_2$ |
| 7 | (5-)CH$_3$ | —CH$_2$—C$_6$H$_3$F$_2$ |
| 5 | (7-)CH$_3$ | —CH$_2$—C$_6$H$_4$—Cl |

The starting substances of the formula (IV) have not yet been disclosed in the literature.

The new nitro-substituted benzothiazole-3-oxides of the general formula (IV) are obtained when corresponding 2-alkylcarbonyl-benzothiazole-3-oxides of the general formula (VIa)

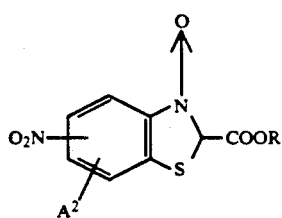

(VIa)

in which

A$^2$ has the abovementioned meaning and

R represents alkyl, preferably having 1 to 4 carbon atoms, are reacted with amines of the general formula (VII)

$$H_2N—A^3 \qquad (VII)$$

in which

A$^3$ has the abovementioned meaning, if appropriate in the presence of diluents, such as, for example, methanol or ethanol, at temperatures between 0° C. and 100° C.

The 2-alkoxycarbonylbenzothiazole-3-oxides of the general formula (VIa) required as intermediates have likewise not yet been disclosed in the literature.

The new 2-alkoxycarbonyl-benzothiazole-3-oxides of the general formula (VIa) are obtained when corresponding 2-chloro-nitrobenzene derivatives of the general formula (VIII)

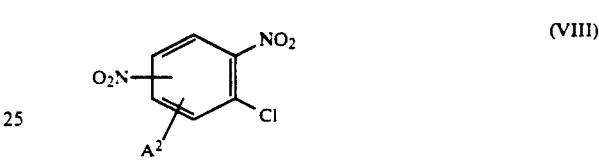

(VIII)

in which

A$^2$ has the abovementioned meaning, are reacted with mercaptoacetic acid esters of the general formula (IX)

$$HS—CH_2—COOR \qquad (IX)$$

in which

R has the abovementioned meaning, in the presence of a base, such as, for example, triethylamine, and in the presence of a diluent, such as, for example, dimethyl sulphoxide, benzene, toluene, tetrahydrofuran, dioxane, methanol, ethanol, propanol, isopropanol and/or water, at temperatures between 0° C. and 100° C., preferably between 20° C. and 80° C.

The starting substances of the formulae (VII), (VIII) and (IX) are known chemicals for organic synthesis.

Process (b) according to the invention for the preparation of the new compounds of the formula (Ia) is preferably carried out using diluents. Possible diluents here are virtually all inert organic solvents. These preferably include aliphatic and aromatic, optionally halogenated hydrocarbons such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers such as diethyl ether and dibutyl ether, glycol dimethyl ether and diglycol dimethyl ether, tetrahydrofuran and dioxane, ketones such as acetone, methyl ethyl ketone, methyl isopropyl ketone and methyl isobutyl ketone, esters such as methyl, acetate and ethyl acetate, nitriles such as, for example, acetonitrile and propionitrile, amides such as, for example, dimethylformamide, dimethylacetamide and n-methyl-pyrrolidone and also dimethyl sulphoxide, tetramethylene sulphone and hexamethylphosphoramide.

The reaction temperatures can be varied within a relatively wide range in process (b) according to the invention. In general, the reaction is carried out at temperatures between 0° C. and 150° C., preferably at temperatures between 20° C. and 100° C.

Process (b) according to the invention is in general carried out at normal pressure.

In order to carry out process (b) according to the invention, the starting substances required in each case are in general employed in approximately equimolar amounts. However, it is also possible to use one of the two components employed in each case in a relatively large excess. The reactions are in general carried out in a suitable diluent and the reaction mixture is stirred for several hours at the temperature required in each case. Working up is in each case carried out by customary methods in the process (b) according to the invention.

The active compounds according to the invention have a strong biological action and can be employed in practice for combating undesired pests. The active compounds are suitable, for example, for use as plant protection agents, in particular for combating fungi.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation:

Pythium species, such as, for example, *Pythium ultimum;*

Phytophthora species, such as, for example, *Phytophthora infestans;*

Pseudoperonospora species, such as, for example, *Pseudoperonospora humuli* or *Pseudoperonospora cubensis;* Plasmopara species, such as, for example, *Plasmopara viticola;*

Peronospora species, such as, for example, *Peronospora pisi* or *P. brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *P. graminea* (conidia form: Drechslera, syn: Helminthosporium);

Cochliobolus species, such as, for example, *Cochliobolus sativus* (conidia form: Drechslera, syn: Helminthosporium);

Uromyces species, such as, for example, *Uromyces appendiculatus;*

Puccinia species, such as, for example, *Puccinia recondita;*

Tilletia species, such as, for example, *Tilletia caries;*

Ustilago species, such as, for example, *Ustilago nuda* or *Ustilago avenae;*

Pellicularia species, such as, for example, *Pellicularia sasakii;*

Pyricularia species, such as, for example, *Pyricularia oryzae;*

Fusarium species, such as, for example, *Fusarium culmorum;*

Botrytis species, such as, for example, *Botrytis cinerea;*

Septoria species, such as, for example, *Septoria nodorum;*

Leptosphaeria species, such as, for example, *Leptosphaeria nodorum;*

Cercospora species, such as, for example, *Cercospora canescens;*

Alternaria species, such as, for example, *Alternaria brassicae* and

Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

The compounds of the formula (I) show in particular strong protective action against Pyricularia species, such as, for example, *Pyricularia oryzae,* which cause damage in rice cultivation, and also against Venturia species, such as, for example, *Venturia inaequalis,* which cause damage in fruit cultivation.

A good action is also observed against Plasmopara and Fusarium species.

Some of the the compounds of the formula (I) also, show an insecticidal and acaricidal action.

The active compounds can be converted into the customary formulations, such as solutions, emulsions, suspensions, powders, foams, pastes, granules, aerosols, very fine capsules in polymeric substances and in coating compositions for seed, as well as ULV formulations.

These formulations are produced in a known manner, for example by mixing the active compounds with extenders, that is, liquid solvents, liquefied gases under pressure, and/or solid carriers, optionally with the use of surface-active agents, that is emulsifying agents and-/or dispersing agents and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water. By liquefied gaseous extenders or carriers are meant liquids Which are gaseous at ambient temperature and under atmospheric pressure, for example aerosol propellants, such as halogenated hydrocarbons as well as butane, propane, nitrogen and carbon dioxide. As solid carriers there are suitable: for example, ground natural minerals, such as kaolins, clays, talc, chalk, quartz, attapulgite, montmorillonite or diatomaceous earth, and ground synthetic minerals, such as highly-disperse silica, alumina and silicates. As solid carriers for granules there are suitable: for example, crushed and fractionated natural minerals such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example, non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products. As dispersing agents there are suitable: for example, lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, as well as in mixtures with fertilizers and other growth regulators.

The active compounds can be used as such or in the form of their formulations or the use forms prepared therefrom, such as ready-to-use solutions, emulsifiable concentrates, emulsions, foams, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seeds of the plants can also be treated In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

USE EXAMPLES

In the following use examples, the compounds shown below were employed as comparison substances:

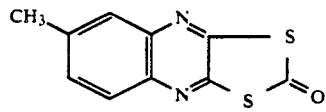

6-methyl-2,3-quinoxalinedithiol cyclocarbonate (quinomethionate) (cf. DE-AS (German Published Specification) 1,100,372),

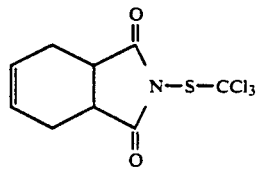

N-trichloromethyl-thio-tetrahydrophthalimide (captan) (cf. U.S. Pat. No. 2,553,770).

EXAMPLE A

Pyricularia test (rice)/protective
Solvent: 12.5 parts by weight of acetone
Emulsifier: 0.3 part by weight of alkylaryl polyglycol ether To produce a suitable preparation of active compound, 1 part by weight of active compound is fixed with the stated amount of solvent, and the concentrate is diluted with water and the stated amount of emulsifier to the desired concentration.

To test for protective activity, young rice plants are sprayed with the preparation of active compound until dripping wet. After the spray coating has dried on, the plants are inoculated with an aqueous spore suspension of Pyricularia oryzae. The plants are then placed in a greenhouse at 100% relative atmospheric humidity and 25° C.

Evaluation of the disease infestation is carried out 4 days after the inoculation.

In this test, a clearly superior activity compared with the prior art is shown, for example, by the compounds shown in Table 1 as Examples No. 1, 2, 4, 5, 11, 13, 17, 23, 26, 27, 31 and 32.

TABLE A

| Pyricularia test (rice)/protective | | |
|---|---|---|
| Active compounds | Active compound conc. in % | Effect as % of the untreated control |
| (known) (quinomethnionate) | 0.025 | 0 |
| (1) | 0.025 | 89 |

TABLE A-continued
Pyricularia test (rice)/protective
| Active compounds | Active compound conc. in % | Effect as % of the untreated control |
|---|---|---|
| 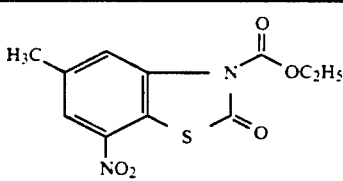 (2) | 0.025 | 89 |
| 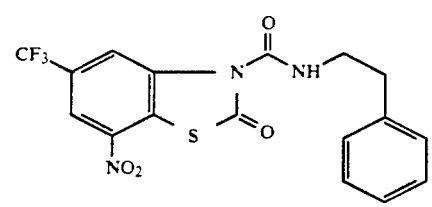 (4) | 0.025 | 100 |
| 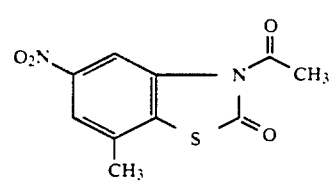 (5) | 0.025 | 90 |
| 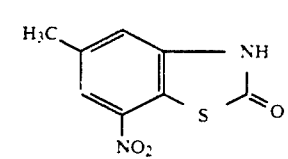 (11) | 0.025 | 100 |
| 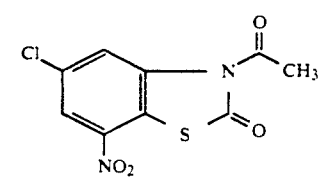 (13) | 0.025 | 89 |
| 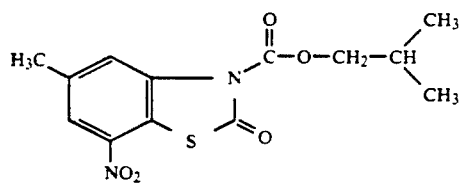 (17) | 0.025 | 89 |
| 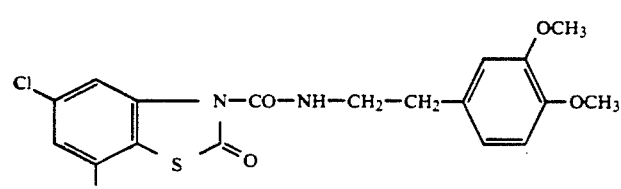 (23) | 0.025 | 80 |

TABLE A-continued

Pyricularia test (rice)/protective

| Active compounds | Active compound conc. in % | Effect as % of the untreated control |
|---|---|---|
| (26) Structure: 4-O₂N, 6-Cl phenyl with N(COCH₃)–C(O)–NH–CH(CH₃)₂ | 0.025 | 90 |
| (27) Structure: 4-O₂N, 6-Cl phenyl with N(COCH₃)–C(O)–NH–CH₂–C₆H₅ | 0.025 | 90 |
| (31) Structure: 4-F₃C, 6-NO₂ phenyl with N(COCH₃)–C(O)–NH–CH₂–C₆H₄–OCH₃ (meta) | 0.025 | 90 |
| (32) Structure: 4-F₃C, 6-NO₂ phenyl with N(COCH₃)–C(O)–NH–CH₂–C₆H₅ | 0.025 | 90 |

EXAMPLE B

Venturia test (apple)/protective
Solvent: 4.7 parts by weight of acetone
Emulsifier: 0.3 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (Venturia inaequalis) and then remain in an incubation cabin at 20° C. and 100% relative atmospheric humidity for 1 day.

The plants are then placed in a greenhouse at 20° C. and a relative atmospheric humidity of about 70%.

Evaluation is carried out 12 days after the inoculation.

In this test, a clearly superior activity compared with the prior art is shown, for example, by the compounds shown in Table 1 as Examples No. 1, 6, 13 and 14.

TABLE B

Venturia test (apple)/protective

| Active compounds | Effect as % of the untreated control at an active compound conc. of 5 ppm |
|---|---|
| known: cyclohexene-dicarboximide N–S–CCl₃ (captan-like) | 51 |
| according to the invention: (1) 4-CH₃, 6-NO₂ phenyl with N(COCH₃)–S–COCH₃ | 85 |
| F₃C, NO₂ phenyl with N(COCH₃)–S–COCH₃ | 100 |

TABLE B-continued

Venturia test (apple)/protective

| Active compounds | Effect as % of the untreated control at an active compound conc. of 5 ppm |
|---|---|

(6)

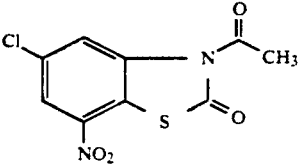

69

(13)

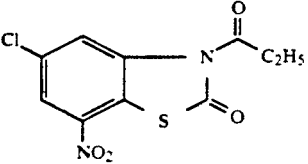

82

(14)

PREPARATION EXAMPLES

EXAMPLE 1

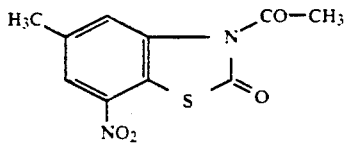

(Process (a))

6.3 g (0.03 mol) of 5-methyl-7-nitro-benzothiazolone and 3.3 g (0.03 mol) of triethylamine are dissolved in 150 ml of acetone. 2.35 g (0.03 mol) of acetyl chloride are allowed to run in slowly dropwise, with stirring, at an internal temperature of 5°–10° C. The reaction mixture is stirred at room temperature for a further 3 hours and then poured onto ice. 6.3 g (83 % of theory) of 3-acetyl-5-methyl-7-nitro-benzothiazolone are obtained in the form of creamcolored flakes of melting point 141° C.

The further compounds of the formula (I) or the formula (Ia) shown in Table 1 hereinabove can also be prepared analogously to Example 1 and in accordance with the general description of the preparation processes (a) and (b) according to the invention.

Starting substances of the formula (IIa)

EXAMPLE (II a-1)

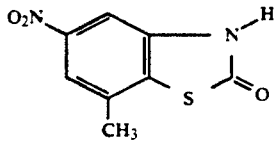

25.3 g (0.1 mol) of 2-carbamyl-5-nitro-7-methylbenzothiazolone-N-oxide are suspended in 150 ml of anhydrous toluene. 16.8 g (0.11 mol) of phosphorus oxychloride are added dropwise to this suspension, with stirring, at an internal temperature of 100° C. and the reaction mixture is heated under reflux for a further 4 hours and allowed to cool. 15.8 g (75 % of theory) of 5-nitro-7-methyl-benzothiazolone of melting point >250° C. are obtained.

The following is obtained analogously:

Example (II a-2)

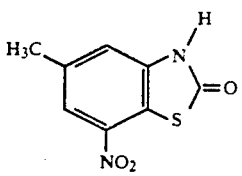

5-methyl-7-nitro-benzothiazolone. Starting substances of the formula (V)

EXAMPLE (V-1)

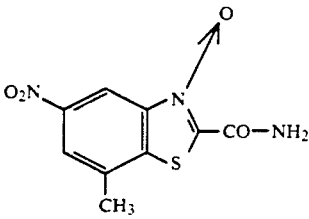

160 g (0.57 mol) of 2-ethoxycarbonyl-5-nitro-7-methyl-benzothiazole-N-oxide are initially introduced in 1.0 l of methanol, 42 g (0.62 mol of $NH_3$) of an aqueous ammonia solution are added and the mixture is stirred at 20° C. to 25° C. for 5 hours. The crystalline product is isolated by filtering off with suction. 140 g (96 % of theory) of 2-carbamyl-5-nitro-7-methyl-benzothiazole-N-oxide of melting point >250° C. are obtained.

It is understood that the specification and examples are illustrative but not limitative of the present invention and that other embodiments within the spirit and scope of the invention will suggest themselves to those skilled in the art.

We claim:

1. A method of combating fungi which comprises applying to such fungi or to a fungus habitat a fungicidally effective amount of 3-acetyl-5-methyl-7-nitrobenzothiazolone of the formula

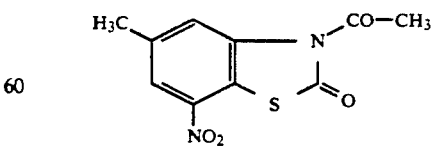

2. A method of combating fungi which comprises applying to such fungi or to a fungus habitat a fungicidally effective amount of 3-phenethylaminocarbonyl-5-trifluoromethyl-7-nitro-benzothiazolone of the formula

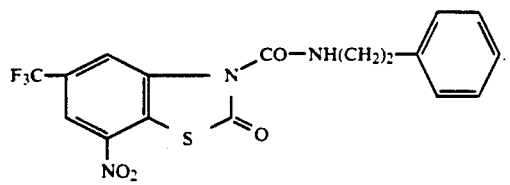
3. A method of combating fungi which comprises applying to such fungi or to a fungus habitat a fungicidally effective amount 3-acetyl-5-trifluoromethyl-7-nitro-benzothiazolone of the formula
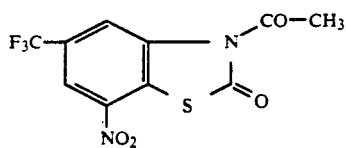
* * * * *